United States Patent [19]

Brisken et al.

[11] 4,442,715
[45] Apr. 17, 1984

[54] VARIABLE FREQUENCY ULTRASONIC SYSTEM

[75] Inventors: Axel F. Brisken, Shingle Springs, Calif.; Lowell S. Smith, Schenectady, N.Y.

[73] Assignee: General Electric Company, Schenectady, N.Y.

[21] Appl. No.: 435,521

[22] Filed: Oct. 20, 1982

Related U.S. Application Data

[63] Continuation of Ser. No. 199,983, Oct. 23, 1980, abandoned.

[51] Int. Cl.³ ............................................. G01N 29/00
[52] U.S. Cl. ........................................ 73/626; 128/660
[58] Field of Search ................ 73/620, 632, 626, 629; 128/660

[56] References Cited

U.S. PATENT DOCUMENTS

| | | | |
|---|---|---|---|
| 2,398,701 | 4/1946 | Firestone | 73/629 |
| 3,453,871 | 7/1969 | Krautkrämer | 73/629 X |
| 3,673,859 | 7/1972 | Couture | 73/632 |
| 3,815,409 | 6/1974 | Macovski | 73/642 X |
| 4,011,747 | 3/1977 | Shaw | 73/620 X |
| 4,145,931 | 3/1979 | Tancrell | 73/626 |
| 4,155,259 | 5/1979 | Engeler | 73/626 |
| 4,155,260 | 5/1979 | Engeler et al. | 73/626 |
| 4,158,308 | 6/1979 | Sharpe et al. | 73/629 X |
| 4,167,879 | 9/1979 | Pedersen | 73/610 |
| 4,180,790 | 12/1979 | Thomas | 73/626 X |
| 4,180,792 | 12/1979 | Lederman et al. | 73/626 X |
| 4,182,173 | 1/1980 | Papadofrangakis | 73/641 X |
| 4,211,948 | 7/1980 | Smith et al. | 73/644 X |
| 4,211,949 | 7/1980 | Brisken et al. | 73/642 X |
| 4,217,909 | 8/1980 | Papadofrangakis | 73/861.25 X |
| 4,257,278 | 3/1981 | Papadofrangakis et al. | 73/861.25 |
| 4,277,978 | 7/1981 | Packette | 73/625 X |
| 4,322,974 | 4/1982 | Abele et al. | 128/660 |
| 4,364,273 | 12/1982 | Redding | 73/611 |

FOREIGN PATENT DOCUMENTS 1074070 6/1967 United Kingdom .
1332898 10/1973 United Kingdom .

OTHER PUBLICATIONS

Ultrasonic Testing of Materials, by Krautkrämer, (1977), pp. 132–136.
Radio Shack Dictionary of Electronics, 1978–1979, p. 473.
Electronics Eng. Handbook, by McGraw-Hill 1975, pp. 12-2 to 12-6.

Primary Examiner—Gerald Goldberg
Assistant Examiner—John E. Chapman, Jr.
Attorney, Agent, or Firm—Donald R. Campbell; James C. Davis, Jr.; Marvin Snyder

[57] ABSTRACT

The ultrasonographer changes the frequency of ultrasound pulses emitted from an ultrasonic transducer as a result of adjusting the RF frequency of the transmitter burst exciting the broadband transducer; this adjustment takes place between pulse transmissions, while examining the patient. In a phased array imager utilizing baseband processing of received echo signals, the same adjustment supplies the corresponding frequency to the demodulator circuits. An alternative method of changing the system spectrum is to have a narrow bandwidth receiver whose center frequency is varied over the available bandwidth.

2 Claims, 10 Drawing Figures

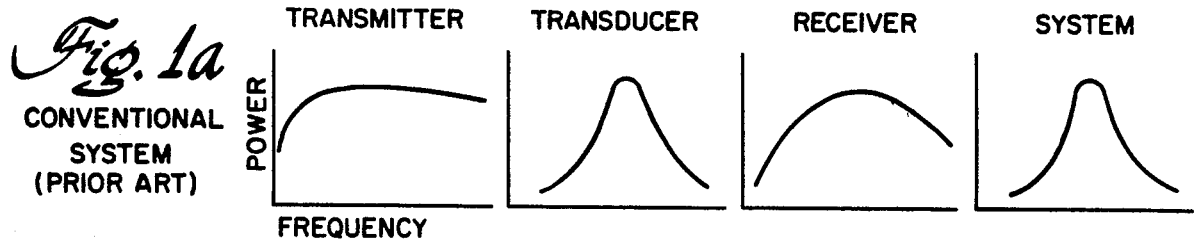
Fig. 1a CONVENTIONAL SYSTEM (PRIOR ART)
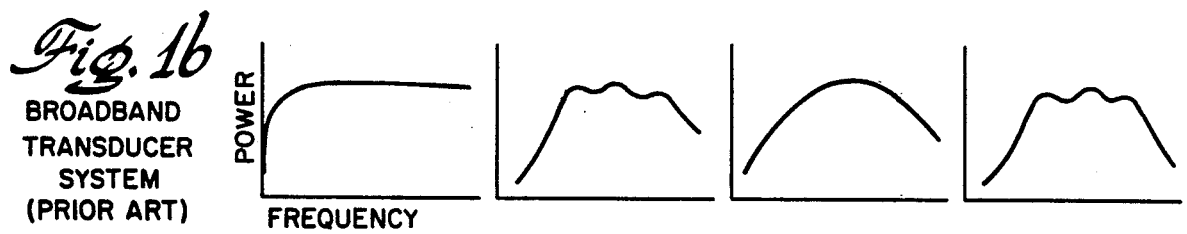
Fig. 1b BROADBAND TRANSDUCER SYSTEM (PRIOR ART)
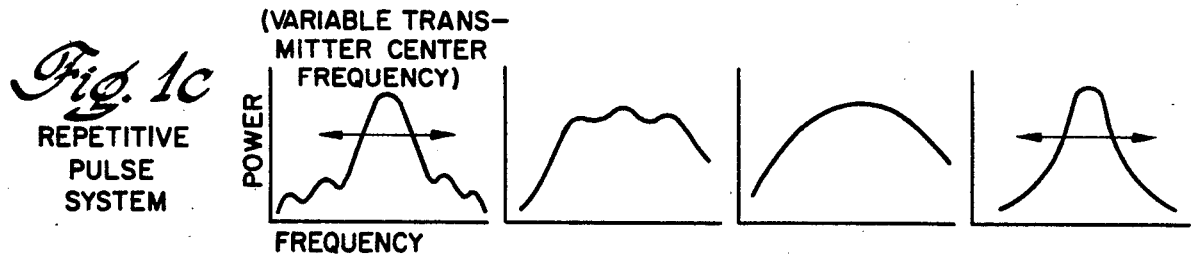
Fig. 1c REPETITIVE PULSE SYSTEM
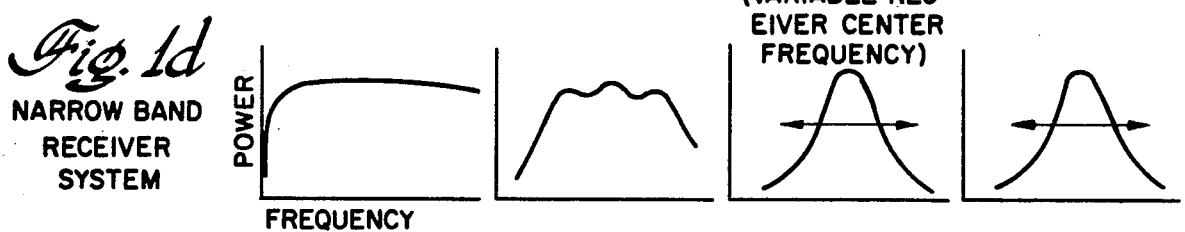
Fig. 1d NARROW BAND RECEIVER SYSTEM
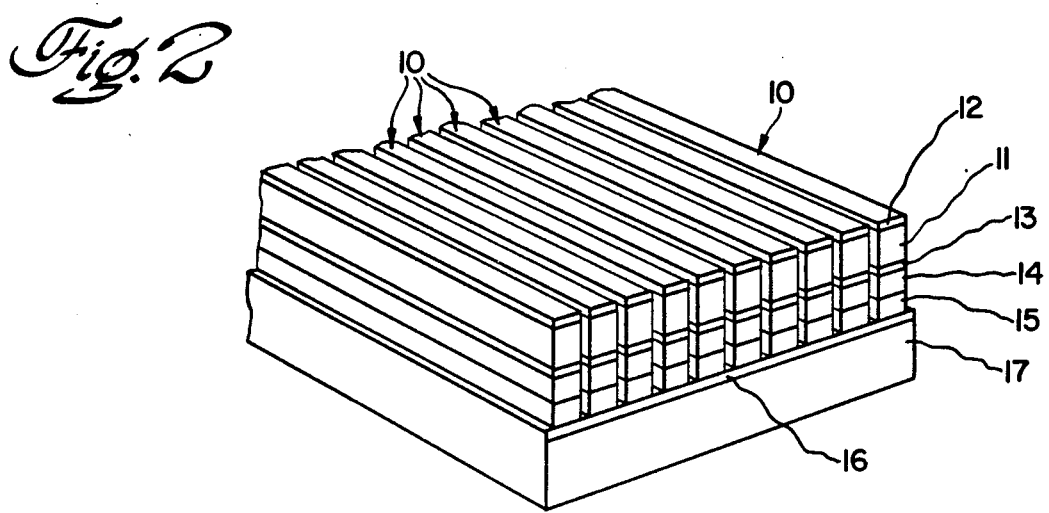
Fig. 2

VARIABLE FREQUENCY ULTRASONIC SYSTEM

This application is a continuation of application Ser. No. 199,983 filed Oct. 23, 1980, now abandoned.

BACKGROUND OF THE INVENTION

This invention relates to ultrasonic imagers and moe particularly to a method of changing the frequency spectrum of the system without changing the transducer or reconfiguring the system.

In ultrasonic examinations, given a specific allowed aperture, the lateral and axial resolution increase linearly (to first order) as a function of frequency. Consequently, a physician may wish to operate with the highest frequency transducers available. Body absorption of ultrasonic energy, however, will result in attenuation of the sound beam at a rate of approximately 1 dB/MHz/cm, the absorption increasing as a linear function of frequency. Furthermoe, various tissues in the body may become specular reflectors at certain frequencies. Thus, real time frequency changes can provide some tissue characterization information. It is consequently advantageous for the clinician conducting the ultrasound examination to be able to adjust the transducer frequency to achieve maximum lateral resolution while echoes from the desired maximum penetration remain just above the noise floor of the system; the examiner may alternatively choose to vary the frequency to enhance or reduce speckle. These adjustments should occur with the transducer or ultrasonic probe on the patient, in real time.

The illustrative embodiment of the ultrasonic imager is an electronic steered beam, single-sector scanner (also known as a phased array system) that has been extensively patented by the present assignee. The following patents and copending applications are among those relevant: U.S. Pat. Nos. 4,155,260; 4,180,790; 4,180,792; 4,182,173; 4,211,948; 4,211,949; 4,217,684; 4,217,909; Ser. No. 094,178 filed on Nov. 14, 1979, now U.S. Pat. No. 4,311,922 C. M. Puckette, "Variable Excitation Circuit"; and Ser. No. 112,852 filed on Jan. 17, 1980, now U.S. Pat. No. 4,277,978 C. M. Puckette, "Adaptive Input Circuit".

SUMMARY OF THE INVENTION

Real time frequency adjustment over a substantial bandwidth is realized between transmission of ultrasound pulses without changing the transducer. This invention can be integrated with many types of ultrasonic imagers including mechanical single element B-scanners, and phased array, annular array, and rectilinear array scanners. The systems are required to have a broadband transducer for transmitting and receiving pulses of ultrasound; the system radiative spectrum is the product of the bandwidths of the transmitter, the transducer, and the receiver. One method of adjusting the system radiative spectrum is to vary the frequency of the emitted ultrasound pulses by exciting the broadband transducer with an RF burst whose frequency is changed; this change occurs between pulse transmissions with the transducer in contact with the patient. This imager is characterized as having a variable narrow bandwidth transmitter and operates into a broadband transducer and either a broadband or variable narrow bandwidth receiver. Another method of adjusting the total system spectrum is to allow the tuning of the receiver to govern the effective system center frequency; such an imager is characterized as having a variable narrow bandwidth receiver and a broadband transmitter and transducer.

The specific imaging system is the steered beam sector scanner previously referred to. The repetitive pulser transmitter frequency is adjustable by the user and the transducer emission center frequency may vary over the entire available bandwidth of typically 2 to 5 MHz for a transducer with a center frequency of 3.5 MHz. The same adjustment changes the frequency references of the baseband signal processing circuits.

BRIEF DESCRIPTION OF THE DRAWINGS

FIGS. 1a-1d show the frequency spectra of the system and system components for two prior art ultrasonic scanners and two scanners of the invention;

FIG. 2 is a partial perspective view of a broadband linear transducer array;

DESCRIPTION OF THE PREFERRED EMBODIMENTS

Figure 3A:
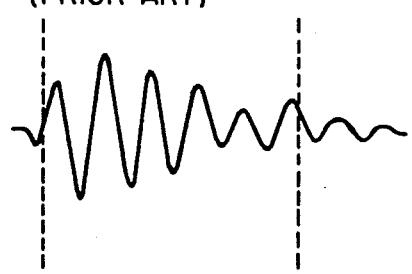
FIGS. 3a and 3b are voltage waveforms for transducers excited with a single impulse (prior art) and an RF burst.

Commercially available ultrasonic systems for medical investigations excite their transducers with electrical "delta functions" or a steeply rising or falling unipolar pulse in an effort to leave the system with the largest possible bandwidth; these prior art systems are usually limited by the narrow bandwidths of their transducers. The typical transducer Q is in the range from 2.5 to 3.0. The four frequency spectrum curves in FIG. 1a represent the frequency spectra of the system components and of the total system. The transmitter and receiver have wide bandwidths, but with a narrow bandwidth transducer, the system spectrum and center frequency are fixed by the transducer and are essentially that of the transducer.

A broadband ultrasonic transducer such as that described in the inventors' U.S. Pat. No. 4,211,948, which is shown in FIG. 2, has a large bandwidth, with values of Q of typically 1.3. Operating these devices with broadband transmitters and receivers (see FIG. 1b) again leaves a resultant system spectrum which is characteristically that of the transducer. In this case, however, the transducer generates a short duration broadband impulse response.

The front surface matched linear phased array in FIG. 2 is capable of performing wide angle sector scans using narrow transducer elements having a width on the order of one wavelength or less at the ultrasound center emission center frequency. This array exhibits high sensitivity, short impulse response, and has a wide field-of-view, and this performance is achieved by the use of impedance matching layers on the front surface of the array and saw cuts from the front surface all the way through the matching layers and piezoelectric ceramic. Every element and matching layer assembly 10 is comprised of a long, narrow ceramic transducer element 11 which has signal and ground electrodes 12 and 13 on opposite faces and a thickness of about one-half wavelength at the emission center frequency. Impedance matching layers 14 and 15 both have a uniform thickness of one-quarter wavelength and serve as acoustic impedance matching transformers. Layer 14 is Pyrex ® borosilicate glass or other glass with the required acoustic impedance, and layer 15 is Plexiglas ® acrylic resin plastic or other plastic with the proper value of acoustic impedance. Transformers 14 and 15 greatly improved energy transfer between the high impedance of the piezoelectric ceramic and the low impedance of the human body or water (the human body is largely water). The front surface matched array can be made with one or three or more impedance matching layers; adequate bandwidths have been achieved with two impedance matching layers. Pressure sensitive Mylar ® tape 16 is placed over the front surface of the array, and a relatively thick body contacting wear plate 17 adheres to the tape. The wear plate is preferably filled silicone rubber (General Electric Company RTV-28); refraction, if it occurs, enhances the field of view and the wear plate does not substantially change the transducer waveform.

With reference to the second tracing in FIG. 1b, a broadband transducer is defined as one in which the bandwidth is greater than 40 percent of the center frequency when the power at any frequency within the band is no less than 6 decibels lower than the power at the frequency of maximum power. FIG. 2 is one example of a broadband ultrasonic transducer, and there are many other configurations including both linear, annular, and single element B-scan transducers.

The repetitive pulse, variable frequency ultrasonic imaging system of FIG. 1c is the preferred embodiment of this invention. The wideband transducer is excited by an RF (radio frequency) burst of typically 3 cycles. The system repetitive pulser frequency is manually adjustable and the transducer frequency is allowed to vary over the entire available bandwidth. Inasmuch as the transmitter now exhibits the narrowest frequency spectrum, assuming a wideband receiver, the system radiative spectrum is that of the transmitter which is similar to the emission spectrum resulting from an effectively narrow bandwidth transducer (FIG. 1a). The emission frequency of the transmitted ultrasound changes and is governed by the transmitter frequency and not by the transducer. This system may be implemented with a variable narrow bandwidth receiver.

Figure 3B:
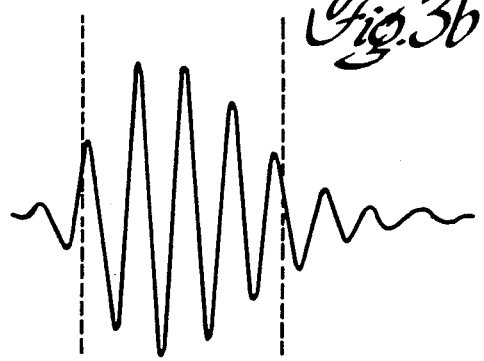

The tendency of the longer excitation, typically three to four complete cycles of voltage, to lengthen the impulse response is compensated by the increased energy in the passband of the transducer. FIG. 3a shows the impulse response resulting from a "delta function" excitation, and FIG. 3b the impulse response from an RF burst of three sine waves. For three cycles from the transmitter, the system sensitivity is observed to increase by approximately 10 dB. It is seen that at the 6 dB levels (between dashed lines), both broadband and narrow band impulse responses exhibit approximately the same duration.

Figure 4:
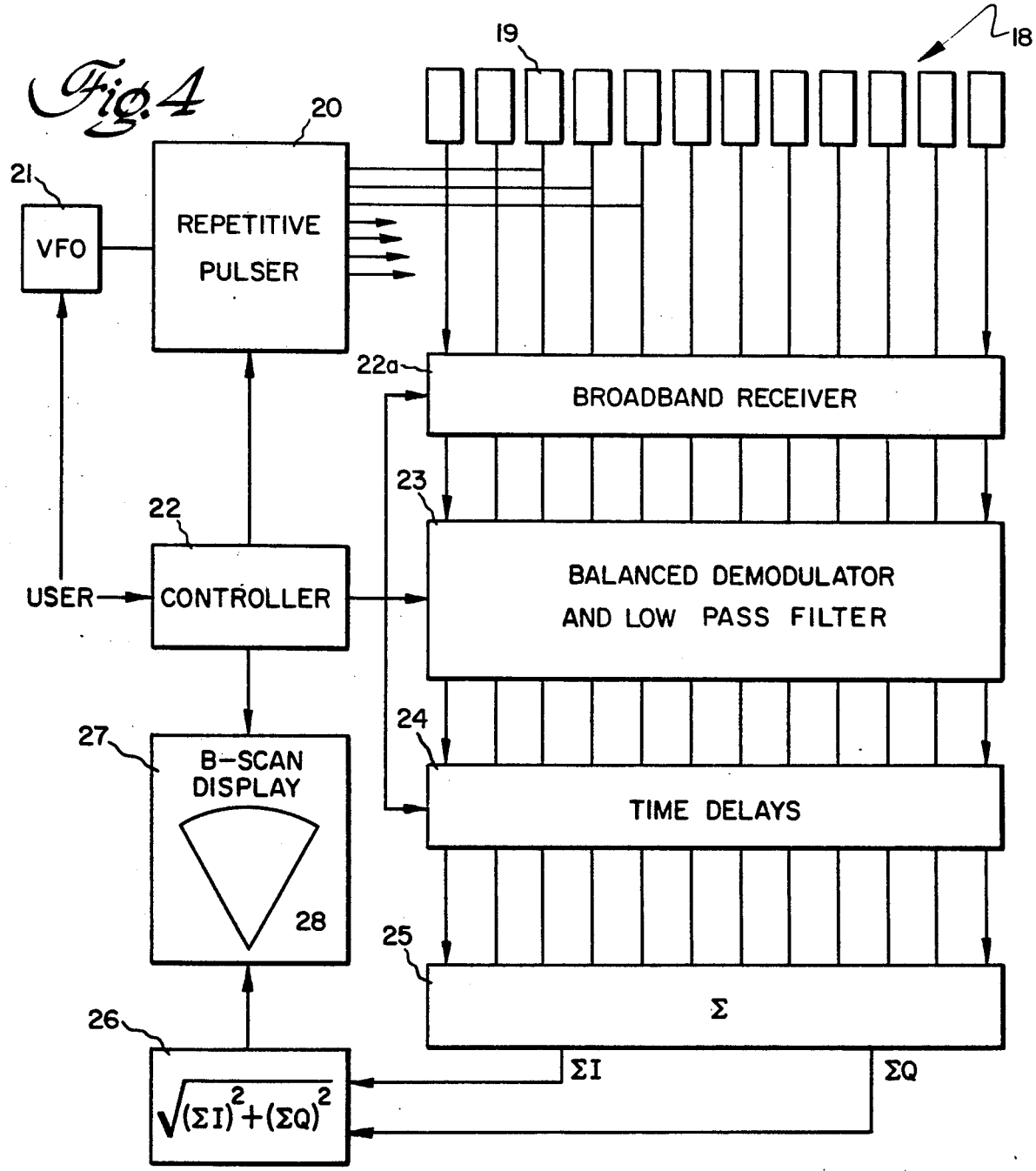
FIG. 4 is a simplified block diagram of the preferred embodiment of the variable frequency phased array system with a repetitive pulser.
Figure 5:
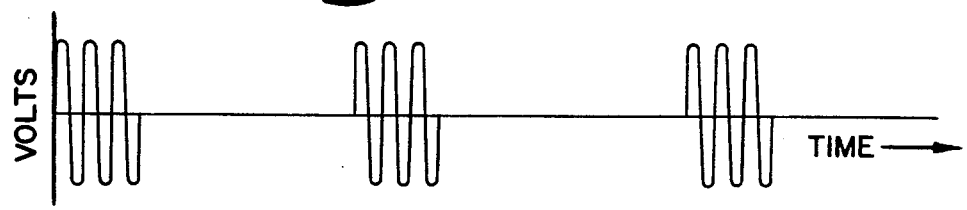
FIG. 5 is a waveform diagram of the excitation bursts generated by the pulser.

The variable frequency, repetitive pulse ultrasonic imager in FIG. 4 is a real time single-sector scanner which features the use of baseband signal processing and is extensively described by the list of patents given previously. Broadband phased transducer array 18 is comprised of a plurality of electroacoustic elements 19 which function dually for transmission and reception. The narrow bandwidth transmitter includes a repetitive gated RF pulser 20 which generates the RF burst excitation voltage with a frequency determined by a user-adjusted variable frequency oscillator 21. The repetition rate of the RF burst is set by controller 22. FIG. 5 is a waveform diagram of the transducer excitation voltage applied to an individual transducer element. Every RF burst has typically three to four complete cycles and the repetition rate of the burst corresponds to the ultrasound pulse transmission rate. The relative element-to-element timing of the RF burst is varied to transmit pulses of ultrasound along different radial scan lines.

The remainder of the system is briefly described and further information is given in U.S. Pat. No. 4,155,260 to W. E. Engeler and J. J. Tiemann, and U.S. Pat. No. 4,217,909 to E. Papadofrangakis and W. E. Engeler, the disclosures of which are incorporated herein by reference. The major components of the receiving channels, which feature baseband signal processing to achieve good lateral resolution while greatly reducing the required time delay accuracy and instead requiring more easily achievable phase focusing accuracy, are a broadband receiver 22a for every channel, a balanced demodulator and low pass filter 23, a time delay device 24, and summers 25. The individual receiving channels have parallel I (in-phase) and Q (quadrature) processing channels in which the received echo signals are electronically steered and dynamically focused. Each signal is amplified and demodulated by a steady transmitter frequency references signal of a phase determined by the path length to the point under examination, and the output of each demodulator is low pass filtered to preserve the envelope and then delayed. Where path lengths differ sufficiently, a delay proportional to the path length difference is also provided before coherent summation. The focused signals, are further processed in circuit 26 to yield a resultant obtained by squaring the I and Q signals, adding together the squared signals, and taking the square root of the sum. This is the video signal which is fed to cathode ray tube 27 where sector-shaped image 28 is built up radial scan line by radial scan line as the transmitted beam direction is changed incrementally.

The repetitive pulser frequency and thus the ultrasound emission frequency is adjusted by the user between pulse transmissions to vary over all or a portion of the entire available bandwidth, typically 2 to 5 MHz for medical examinations with a 3.5 MHz center frequency transducer. The image appearing on display device 27 is observed by the physician in order to arrive at the best setting. The same adjustment also supplies the correct frequency, i.e., the correct emission frequency reference signal, to demodulator circuits 23. With reference to FIG. 5 of U.S. Pat. No. 4,155,260, the frequency adjustment is presented to master oscillator 65 and the associated frequency synthesizers.

Figure 6:
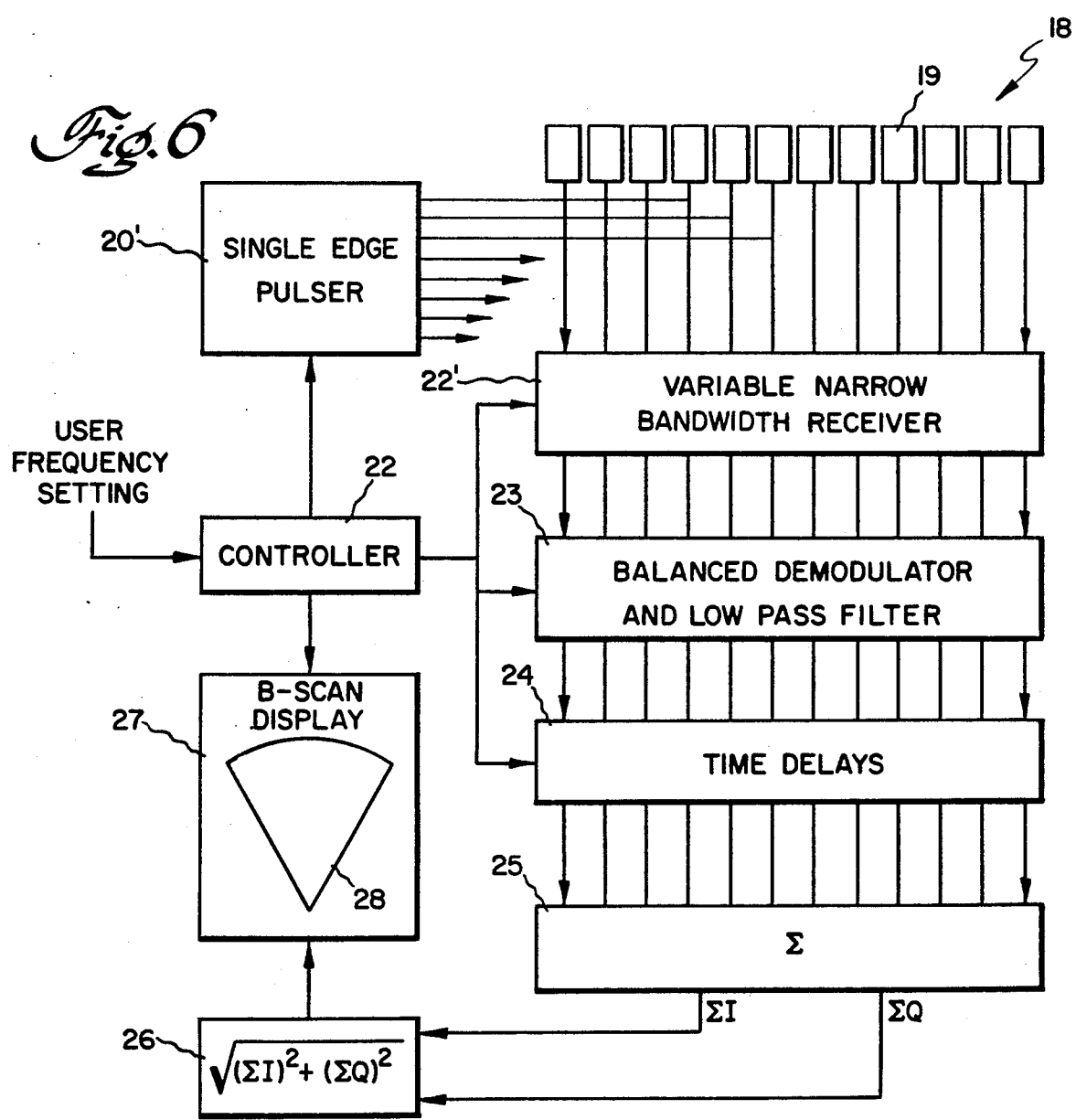
FIG. 6 is a block diagram of another variable frequency phased array system with a narrow bandwidth receiver.

An alternative to a system with a narrow bandwidth transmitter, FIG. 1c, is the narrow bandwidth receiver system represented by the spectra of FIG. 1d. The tuning of the receiver governs the system center frequency. Only the differences between FIG. 4 and FIG. 6, which is a variable frequency phased array system with a narrow bandwidth receiver, will be commented upon here. The broadband transmitter includes a conventional single edge pulser 20' which applies unipolar pulse excitation voltage to the transducer element, the same as the second prior art system, FIG. 1b. The user's frequency setting is fed through the controller 22 to the variable narrow bandwidth receiver 22'. The L and C tuning components of the receiver circuitry are adjusted between pulse transmissions to vary the receiver center frequency. This is diagrammed by the third tracing in FIG. 1d. Thus, the tuning of the receiver determines the center frequency of the total system spectrum, defined as the product of the bandwidths of the transmitter, the transducer, and the receiver. This technique is less than optimal in that much of the ultrasonic energy in the body is filtered out at the receiver and lost. As limits for the maximum ultrasonic energy in the human body are approached, this technique will be less sensitive than that base on transmitter filtering, that is, repetitive pulsing.

While the invention has been particularly shown and described with reference to several preferred embodiments thereof, it will be understood by those skilled in the art that various changes in form and details may be made therein without departing from the spirit and scope of the invention.

The invention claimed is:

1. In a steered beam, sector scan ultrasonic imaging system for medical examinations comprising a broadband linear phased array transducer having plural electroacoustic elements for transmitting pulses of ultrasound and for receiving echo signals, said transducer having a bandwidth greater than 40 percent of the center frequency when the power at any frequency in the band is no less than 6 decibels lower than the power at the frequency of maximum power, a transmitter for producing transducer excitation voltages which are fed to selected elements in sequence, a multichannel broadband receiver, a plurality of receiving channels each having an in-phase and a quadrature channel in which said echo signals are coherently demodulated using emission frequency reference signals and are focused and summed to produce focused in-phase and quadrature signals, and a B-scan display device, said system having a radiative spectrum that is the product of the bandwidths of said transducer, transmitter, and receiver, the method of adjusting the system radiative spectrum which comprises:

varying the emission frequency of the pulses of ultrasound between 2 and 5 megahertz, while examining the patient without changing said transducer, by exciting selected elements in sequence with an RF burst whose frequency is changed only between pulse transmissions, said RF burst frequency being varied over all or a portion of the transducer bandwidth; and adjusting said receiving channel frequency reference signals between pulse transmissions to correspond with the RF burst frequency.

2. The method of claim 1 wherein every RF burst has about three complete cycles of voltage.

* * * * *